US00PP14322P29

(12) United States Plant Patent
Hanes

(10) Patent No.: US PP14,322 P2
(45) Date of Patent: Nov. 25, 2003

(54) PETUNIA PLANT NAMED 'WHIP SCARL'

(50) Latin Name: *Petunia hybrida*
Varietal Denomination: Whip Scarl

(75) Inventor: Mitchell Eugene Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 10/389,075
(22) Filed: Mar. 13, 2003
(51) Int. Cl.[7] ..... A01H 5/00
(52) U.S. Cl. ..... Plt./356
(58) Field of Search ..... Plt./356

*Primary Examiner*—Kent Bell
(74) *Attorney, Agent, or Firm*—Jondle & Associates, PC

(57) ABSTRACT

A petunia cultivar particularly distinguished by scarlet colored flowers, compact habit and good basal branching.

1 Drawing Sheet

Genus and species: *Petunia hybrida.*
Variety denomination: 'Whip Scarl'.

BACKGROUND OF THE NEW PLANT

The present invention comprises a new and distinct cultivar of petunia, botanically known as *Petunia hybrida,* and hereinafter referred to by the cultivar name 'Whip Scarl'. The new cultivar is asexually reproduced from vegetative cuttings and tissue culture resulting from the cross of the seed/pod parent 99-189-1, a red proprietary line that is unnamed and unpatented×99-1-4, a purple proprietary line that is unnamed and unpatented.

'Whip Scarl' is a product of a planned breeding program intended to create new petunia plants with scarlet colored flowers, compact habit, good basal branching and moderately vigorous growth.

The new cultivar was created in 1999 in Gilroy, Calif. and has been asexually reproduced repeatedly by vegetative cuttings and tissue culture in Gilroy, Calif., Andijk, The Netherlands, and Guatemala over a three-year period. The plant has also been trialed at Gilroy, Calif., Litchfield, Mich. and Andijk, The Netherlands. The present invention has been found to retain its distinctive characteristics through successive asexual propagations; and this novelty is firmly fixed.

DESCRIPTION OF PHOTOGRAPH

This new petunia plant is illustrated by the accompanying photograph which shows blooms, buds, and foliage of the plant in full color, the colors shown being as true as can be reasonably obtained by conventional photographic procedures.

The photograph shows the mature flowers.

DESCRIPTION OF THE NEW CULTIVAR

The following detailed descriptions set forth the distinctive characteristics of 'Whip Scarl'. The data, which defines these characteristics, were collected from asexual reproductions carried out in Gilroy, Calif. The plant history was taken on 10 months old plants grown in one-gallon pots in fall/winter season, in a poly-covered greenhouse under 2–4 hours supplemental light and color readings were taken in the greenhouse in the winter season under natural light. Plants had been cut back numerous times prior to data readings being taken. Color references are primarily to The R.H.S. Colour Chart of The Royal Horticultural Society of London (R.H.S.). Texture description details were observed under a dissecting microscope according to The New Royal Horticultural Society Dictionary of Gardening (1992).

THE PLANT

Classification:
*Botanical.*—Petunia hybrida.
*Commercial.*—Petunia.
Form: Semi upright and decumbent.
Growth and branching habit: Good vigorous habit, well-branched, full plant.
Height: From soil level to top of blooms: Approximately 10–15 cm.
Width: Approximately 45–55 cm including flowers.
Time to produce a finished flowering plant: 9–11 weeks.
Outdoor plant performance: Full sun; free flowering through the summer; some heat tolerance; Used as a hanging plant, in mixed container plantings, and mass planting in a bed.
Time to initiate roots: Approximately 18–23 days in the greenhouse.
Root description: Fibrous, white.

THE LEAVES

Arrangement: Alternate, upper leaves sub-opposite.
Length: 4.0–4.5 cm.
Width: 2.8–3.6 cm.
Leaf blade shape: Ovate.
Leaf margin: Entire.
Apex aspect: Acute.
Base aspect: Acuminate.
Leaf color: Upper side; RHS 137A (green); Underside; RHS 146B (yellow-green).
Texture: Glandular hairs.
Venation: Palmate.
Venation color: RHS 144A (yellow-green).
Petiole length: 0.8–1.0 cm.
Petiole width: 0.25 cm.
Petiole color: RHS 144A (yellow-green).
Petiole texture: Glandular hairs.

THE STEM

Length: 40–50 cm.
Diameter: 0.3–0.04 cm.
Internode length: 1.3–2.5 cm.
Color: RHS 144B (yellow-green).
Texture: Glandular hairs.
Stem anthocyanin: None.
Peduncle color: RHS 144B (yellow-green).
Peduncle length: 2.3–2.7 cm.
Peduncle diameter: 0.15–0.2 cm.
Peduncle texture: Glandular hairs.

THE BUD

Shape: Oblong.
Diameter: 0.6 cm.
Length: 2.5–3.0 cm.
Color at tight bud: RHS 176B (greyed-orange).

THE FLOWER

Blooming habit: Continuous all through the growing season. Good floriferousness.
Inflorescence type: Flowers solitary in upper leaf axis.
Young flower color: RHS 46B (red) and RHS 45A (red) 'mingled' base color; RHS 183A (greyed-purple) mid-veins; RHS 46A (red) secondary veins.
Young flower floret diameter: 3.7–4.0 cm.
Mature flower color: Upper side, RHS 47B (red) base color; close to RHS 46A (red) mid-veins; RHS 46B (red) secondary veins. Underside, RHS 50C (red) base color; RHS 146C (yellow-green) mid-veins; RHS 47D (red) secondary veins.
Corolla tube colors inside: RHS N155C (white) base color; RHS 166B (greyed-orange) mid-veins, RHS 166C (greyed-orange) secondary veins.
Corolla tube length: 2.5–2.8 cm.
Corolla outside texture: Many glandular hairs.
Floret form and number of petals: Funnel form, 5 lobed petals fused at base; calyx, 5 deeply lobed.
Flower (limb) diameter: 4.5–4.8 cm.
Petal apex shape: Mucronulate.
Petal base shape: Fused.
Petal margin: Entire.
Waviness of petals: Moderate.
Petal lobation: Moderate.
Petal texture: Papillose; shiny sheen.
Sepals: 5, fused at the base.
Sepal color: RHS 137A (green).
Sepal length: 1.3–1.5 cm.
Sepal width: 0.3–0.4 cm.
Sepal shape: Oblong.
Sepal apex: Acute/Obtuse.
Sepal texture: Many glandular hairs.
Lastingness of individual blooms: 4–8 days.
Fragrance: None.

THE REPRODUCTIVE ORGANS

Stamens: 5; 2 taller, 2 short, 1 much shorter.
Filament color: RHS 155B (white).
Pollen color: RHS 158A (yellow-white).
Pistil: One.
Stigma: RHS 144B (yellow-green).
Style color: RHS 145C (yellow-green).
Fruit seed set: Not observed.

DISEASE AND INSECT RESISTANCE

Not observed.

COMPARISON WITH KNOWN CULTIVARS

'Whip Scarl' differs from the female parent 99-189-1 in the following ways: The female parent is an upright growing, late flowering, and red flowers of medium size. 'Whip Scarl' is earlier flowering, moderately vigorous plant, with larger scarlet flowers.

'Whip Scarl' differs from the male parent 99-1-4 in the following ways: The male parent is a later flowering, trailing plant with purple flowers. 'Whip Scarl' is an earlier flowering, more free flowering plant with scarlet flowers.

I claim:

1. A new and distinct petunia plant as shown and described herein.

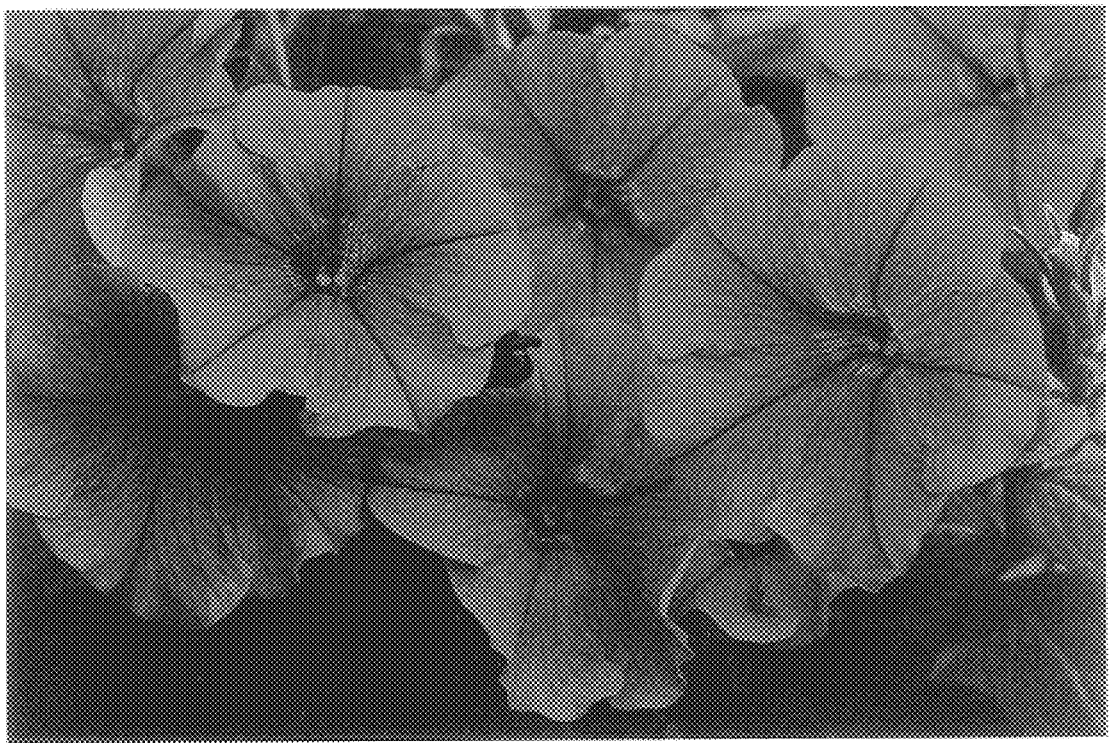

* * * * *